United States Patent
Radicke et al.

(10) Patent No.: US 12,383,210 B2
(45) Date of Patent: Aug. 12, 2025

(54) METHOD AND SYSTEM FOR CONTROLLING AN FFS X-RAY SYSTEM

(71) Applicant: Siemens Healthcare GmbH, Erlangen (DE)

(72) Inventors: Marcus Radicke, Veitsbronn (DE); Ralf Nanke, Neunkirchen am Brand (DE); Steffen Kappler, Effeltrich (DE); Thomas Weber, Hausen (DE); Ferdinand Lueck, Erlangen (DE); Ludwig Ritschl, Buttenheim (DE); Anja Fritzler, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 268 days.

(21) Appl. No.: 18/146,704

(22) Filed: Dec. 27, 2022

(65) Prior Publication Data

US 2023/0200754 A1 Jun. 29, 2023

(30) Foreign Application Priority Data

Dec. 29, 2021 (EP) .................... 21218102

(51) Int. Cl.
*A61B 6/02* (2006.01)
*A61B 6/00* (2006.01)
(Continued)

(52) U.S. Cl.
CPC ............... *A61B 6/025* (2013.01); *A61B 6/02* (2013.01); *A61B 6/4021* (2013.01);
(Continued)

(58) Field of Classification Search
CPC ..... A61B 6/025; A61B 6/4021; A61B 6/4028; A61B 6/44; A61B 6/4429; A61B 6/4435;
(Continued)

(56) References Cited

U.S. PATENT DOCUMENTS

| 5,644,612 A * | 7/1997 | Moorman | A61B 6/4488 378/146 |
| 7,869,571 B2 * | 1/2011 | Hsieh | A61B 6/032 378/124 |

(Continued)

FOREIGN PATENT DOCUMENTS

DE 102018221559 A1 6/2020

OTHER PUBLICATIONS

Kachelriess, M. et al: "Flying focal spot (FFS) in cone-beam CT"; IEEE Transactions on Nuclear Science; vol. 53; No. 3, 1. Jun. 2006; pp. 1238-1247; XP055114678; ISSN: 0018-9499; DOI: 10.1109/TNS.2006.874076; 2006.

*Primary Examiner* — Allen C. Ho
(74) *Attorney, Agent, or Firm* — Harness, Dickey & Pierce, P.L.C.

(57) ABSTRACT

A method for controlling an FFS X-ray system comprises: simulating a beam geometry of the X-ray beam at a specified FFS deflection onto the detector during recording of a projection image; determining whether cross-radiation is present in a region around the detector by the simulated beam geometry of the X-ray beam; generating FFS control data for the recording of the projection image, wherein the FFS control data either (i) causes FFS deflection that is reduced relative to the specified FFS deflection for the recording of the projection image in the event of the cross-radiation being present for the recording of the projection image or (ii) causes the specified FFS deflection otherwise; repeating the simulating, the determining and the generating FFS control data for at least one further recording of a projection image; and generating a control data set including the FFS control data, for controlling an FFS X-ray system.

21 Claims, 3 Drawing Sheets

(51) Int. Cl.
  *A61B 6/40* (2024.01)
  *A61B 6/50* (2024.01)
  *H05G 1/08* (2006.01)
  *H05G 1/26* (2006.01)
  *H05G 1/30* (2006.01)
  *H05G 1/52* (2006.01)
  *H05G 1/60* (2006.01)

(52) U.S. Cl.
  CPC .......... *A61B 6/4028* (2013.01); *A61B 6/4452* (2013.01); *A61B 6/483* (2013.01); *A61B 6/486* (2013.01); *A61B 6/502* (2013.01); *A61B 6/5205* (2013.01); *A61B 6/5258* (2013.01); *A61B 6/5282* (2013.01); *A61B 6/54* (2013.01); *A61B 6/542* (2013.01); *A61B 6/545* (2013.01); *H05G 1/08* (2013.01); *H05G 1/26* (2013.01); *H05G 1/30* (2013.01); *H05G 1/52* (2013.01); *H05G 1/60* (2013.01)

(58) Field of Classification Search
  CPC ..... A61B 6/4447; A61B 6/4452; A61B 6/483; A61B 6/486; A61B 6/487; A61B 6/502; A61B 6/52; A61B 6/5205; A61B 6/5211; A61B 6/5258; A61B 6/5282; A61B 6/54; A61B 6/542; A61B 6/545; H05G 1/08; H05G 1/26; H05G 1/265; H05G 1/28; H05G 1/30; H05G 1/52; H05G 1/60
  USPC ........ 378/7, 26, 37, 62, 98.6, 137, 143, 144, 378/22, 25, 113
  See application file for complete search history.

(56) References Cited

U.S. PATENT DOCUMENTS

| | | | |
|---|---|---|---|
| 8,189,742 B2* | 5/2012 | Behling | H01J 35/26 378/124 |
| 8,457,282 B2* | 6/2013 | Baorui | A61B 6/502 378/22 |
| 8,515,005 B2* | 8/2013 | Ren | A61B 6/025 378/146 |
| 8,571,181 B2* | 10/2013 | Charette | H01J 35/06 378/136 |
| 8,767,911 B2 | 7/2014 | Ren et al. | |
| 8,923,484 B2* | 12/2014 | Zou | H01J 35/28 378/126 |
| 9,517,041 B2* | 12/2016 | Melman | A61B 6/107 |
| 9,895,124 B2* | 2/2018 | Fujii | A61B 6/5205 |
| 9,968,313 B2* | 5/2018 | Melman | A61B 6/542 |
| 11,177,105 B2* | 11/2021 | Travish | A61B 6/51 |
| 11,633,168 B2* | 4/2023 | Liu | A61B 6/035 378/9 |
| 11,779,297 B2* | 10/2023 | Nakayama | A61B 6/482 378/37 |
| 12,154,751 B2* | 11/2024 | Radicke | A61B 6/582 |
| 12,156,321 B2* | 11/2024 | Weber | H01J 35/153 |

* cited by examiner

METHOD AND SYSTEM FOR CONTROLLING AN FFS X-RAY SYSTEM

CROSS-REFERENCE TO RELATED APPLICATION(S)

The present application claims priority under 35 U.S.C. § 119 to European Patent Application No. 21218102.8, filed Dec. 29, 2021, the entire contents of which are incorporated herein by reference.

FIELD

One or more example embodiments of the present invention relate to a method and a control facility for controlling an FFS X-ray system, preferably for tomosynthesis. In particular, one or more example embodiments of the present invention relate to the control of FFS deflection and collimator apertures of an X-ray source.

BACKGROUND

In recent years, a method known as "flying focal spot" (FFS) has been used in tomographic methods of X-ray diagnosis. In this method, the electron beam of an X-ray source emitted by the cathode is deflected by a magnetic field, generated, for example, by a magnetic coil, before it hits the anode. This can change the point of impact of the electron beam on the anode surface. FFS is, inter alia, used in mammography.

The principle of FFS can be used to selectively sweep an X-ray beam over a region or to compensate spatial deviation of an X-ray beam. To achieve a periodic movement of the X-ray beam, the magnetic coil can be exposed to a periodic deflection current. At present, a deflection current is often assumed to be a periodic function with a period length of, for example, 200 ms (for example, as a sawtooth function).

In the case of a moving X-ray source, such as is used, for example, for tomosynthesis in mammography, FFS in particular has the function of compensating the mechanical movement of the X-ray source in space during the exposure time of an object (for example 40 ms or 70 ms) by moving the focal spot in the opposite direction so that it appears stationary during a projection.

In the case of a rotating X-ray source, with or without the use of FFS, the problem can arise that cross-radiation of peripheral regions takes place, i.e., that the X-ray beam irradiates regions other than the detector that should not be irradiated. Although the detector is surrounded by a peripheral region which can definitely be hit by X-rays, no radiation should extend beyond this region, since it may hit a person there.

For example, in breast tomosynthesis, the X-ray source moves in a circular arc over the detector. During this time, the arms of the patient being examined are usually positioned to the right and left of the support on which the breast is being examined. If the X-ray beam extends beyond the edges of the support (i.e., beyond the edges of the detector or possibly beyond the peripheral regions thereof), lateral cross-radiation of the detector occurs and the arms are exposed and the patient would receive an adverse dose there.

In conventional systems, this problem is counteracted with apertures. These apertures are often collimator plates and limit the beam cone of the X-ray beam to a predefined region on the detector. However, when using FFS, the focal point shifts relative to the aperture, which in turn could result in cross-radiation onto unwanted regions.

SUMMARY

It is an object of one or more example embodiments of the present invention to provide an improved method and a corresponding system for controlling an FFS X-ray system with which at least the above-described disadvantages may be avoided and in particular cross-radiation can be suppressed and/or prevented.

This object may be achieved by a method, a control data set, a system and/or an X-ray system according to one or more example embodiments of the present invention.

The method according to one or more example embodiments of the present invention is used to control an FFS X-ray system. An FFS X-ray system (i.e., an X-ray system with a "flying focal spot") is known in principle to the person skilled in the art and, in addition to an X-ray source, comprises an (X-ray) detector for detecting the radiation emitted by the X-ray source and an FFS deflection coil for deflecting the electron beam in the X-ray source in a deflection direction. The X-ray source is preferably an FFS X-ray source comprising a cathode, an anode and additionally the FFS deflection coil as functional elements. Herein, the FFS deflection coil can be arranged inside or outside the vacuum housing (of the X-ray tube) of the X-ray source.

The deflection direction means a positive FFS deflection (in one direction) and a negative FFS deflection (in the other direction). If current flows through the FFS deflection coil, it induces a magnetic field and the electron beam is deflected (transverse to its direction of movement) according to the Lorentz force. In the case of a positive current, the FFS deflection takes place in one direction, in the case of a negative current (reversed polarity), the FFS deflection takes place in the opposite direction.

Herein, the X-ray source is guided in a circular movement around the detector to produce a plurality of projection images. To record the projection images, an X-ray beam collimated by a collimator aperture is switched on and off many times during the circular movement. Each time the X-ray source is switched on and its X-ray beam falls onto the detector, a new projection image can be recorded. Herein, during FFS deflection, the X-ray beam can be influenced by the FFS deflection coil in that the focal point of the electron beam generating the X-ray beam is deflected between the cathode and anode of the X-ray source.

The method comprises the following steps:
  simulating a beam geometry of the X-ray beam at a specified FFS deflection onto the detector during recording of a projection image,
  determining whether cross-radiation is present in a predetermined region around the detector by the simulated X-ray beam,
  generating FFS control data for the recording, which, in the event of cross-radiation being present for the recording, causes FFS deflection that is reduced relative to the specified FFS deflection for this recording, and otherwise causes the specified FFS deflection,
  repeating the steps for at least one further recording,
  generating a control data set comprising the generated FFS control data for controlling an FFS X-ray system.

If the positions of the focal point, collimator aperture (the aperture opening is known) and detector (the dimensions of which are known) are known, beam geometry is comparatively easy to simulate, since it is basically only necessary to construct a cone from the focal point which is limited by the collimator aperture and to determine the surface region covered by the cone in the plane of the detector. This surface region is the "region irradiated" by the X-ray beam in the plane of the detector. Ultimately, it is this irradiated region that is important. It should be added that the collimator aperture should usually be adjusted so that only the region of the detector on which breast tissue is also projected is irradiated.

However, it should be noted that the X-ray source, and thus also the focal point and the collimator aperture, move on a circular path during recording. During recording, these elements are not in a fixed recording position, but move on a circular arc path. Furthermore, the focal point additionally moves relative to the collimator aperture during FFS deflection. All this has to be taken into account in the simulation. Incidentally, "simulation" means any kind of determination that does not correspond to a direct measurement. The beam geometry can be calculated from geometric data but can also, for example, be looked up in a look-up table. It is also possible to use measurement data from a past examination.

Since, ultimately, cross-radiation is to be determined and thus the aforementioned irradiated region is to be determined, the simulation can relate to discrete points in time during the recording, for example at the start of the recording and at the end, possibly with some calculations for time points in between. Ultimately, it is advantageous for the maximum irradiated region to be determined, in particular with information about which dose was deposited where. If necessary, the dose can be derived directly from the intensity of the X-ray beam.

Since the surface of the detector is known, it can be determined whether the irradiated region was located completely on the detector or extended beyond this during recording. It should be noted that the detector is often surrounded by a peripheral region that is used for support and also for radiation protection. This region is usually made of a material that is transparent to radiation, for example GRP. Parts of a person often lie directly on this region, for example the arms of a patient during mammography. Here, the detector surface can, for example, be selected as the predetermined region (if it is generally desired to prevent cross-radiation of the detector) or the surface of the detector plus the peripheral region (if it is only desired to prevent body parts from being exposed).

Since the irradiated region is known from the simulation and the predetermined region is known, cross-radiation can be easily determined by looking whether the irradiated region is always located within the predetermined region or extends beyond this during recording.

If the irradiated region additionally enables information about which dose was deposited where, it is even possible to determine which dose was deposited at which location during cross-radiation.

A decision is now made as to whether or not cross-radiation is present. This is preferably achieved by determining whether simulated X-ray beams are located outside the predetermined region and in particular additionally whether the intensity there due to the simulated X-ray beams is above a predetermined threshold. A threshold can, in particular, relate to a prespecified measurement for a surface or a dose and/or specified regions (for example where parts of a person's body could be located). Therefore, it can, for example, be determined whether the irradiated surface extending beyond the predetermined region is greater than a specific surface measure (possibly even zero) or it can be determined whether the dose deposited outside the predetermined region is greater than a threshold value. However, it can also be determined whether a specific dose was deposited on a specific surface (for example a patient's arms).

This knowledge about the cross-radiation is now used as the basis for the generation of the FFS control data for the control data set. This control data set could also be referred to as the "FFS control data set" since the FFS control data is constructed to cause FFS deflection. Since, however, this control data set can also comprise further control data, for example beam control data or aperture control data, as will be explained in more detail below, the term "control data set" will continue to be used.

The FFS control data for a recording is normally constructed to cause the specified FFS deflection. This can in particular be the same for each recording (of a projection image), for example in that the focal point is stationary relative to the detector during recording.

However, two cases are now distinguished according to the method according to one or more example embodiments of the present invention, namely whether or not cross-radiation is present. The fact that cross-radiation is present can (as stated above) in particular be established using a predetermined threshold.

If a specific cross-radiation is present, FFS control data for an FFS deflection that is reduced relative to the specified FFS deflection is generated for the relevant recording (of a projection image), if not, FFS control data for the specified FFS deflection is generated.

This is then repeated for at least one further recording (of a projection image), in particular for the recording of all projection images. Herein, the calculations should preferably be performed at least for large angles relative to the vertical above the detector, since the risk of cross-radiation is greatest there.

Then, the control data set is created from the generated FFS control data (specified and possibly reduced) for controlling an FFS X-ray system. This can be used directly for controlling the FFS X-ray system, or, however, it can be saved and used to control an FFS X-ray system with a similar or identical structure. However, it should be noted that the collimator aperture is sometimes set individually for each patient (during mammography, the collimator setting may depend on the current breast size) or there are different exposure times for each projection image (the longer the exposure time, the greater the maximum deflection of the FFS) so that the method is preferably performed before an examination after setting the collimator aperture or selecting the exposure time.

A control data set created via this method is also covered by one or more example embodiments of the present invention. For example, the method could be performed for a plurality of possible aperture openings and the data set resulting therefrom used for FFS X-ray systems, wherein after the collimator aperture has been set, the corresponding control data is simply selected according to the collimator aperture setting.

A system according to one or more example embodiments of the present invention is used (like the method) to control an FFS X-ray system with an X-ray source, which is guided in a circular movement around a detector to produce a plurality of projection images, wherein an X-ray beam collimated by a collimator aperture is turned on and off many times during the movement, and wherein, for FFS deflection, the FFS X-ray system comprises an FFS deflection coil with which a focal point of an electron beam generating the X-ray beam can be deflected between the cathode and anode of the X-ray source. The system comprises the following components:

a simulation unit configured to simulate a beam geometry of the X-ray beam at a specified FFS deflection onto the detector during recording of a projection image, a determining unit configured to determine whether cross-radiation is present in a predetermined region around the detector by the simulated X-ray beam, a control data unit configured to generate a control data set according to one or more example embodiments of the present invention.

The mode of operation of the units has already been described in detail in the context of the method. To move a collimator aperture, the system can also have a special moving unit. However, an FFS X-ray system with a collimator aperture that can be moved by automation or automated means usually has a moving unit, for example, an electric motor with a gear that can be easily actuated with control signals.

An FFS X-ray source according to one or more example embodiments of the present invention comprises a control facility (or controller) and a system according to one or more example embodiments of the present invention, which can certainly be present in the control facility. Alternatively or additionally, the FFS X-ray source, or the control facility thereof, can also comprise a control data set according to one or more example embodiments of the present invention, for example in a memory unit.

A control facility (or controller) for an X-ray system according to one or more example embodiments of the present invention comprises a system according to one or more example embodiments of the present invention or a control data set according to one or more example embodiments of the present invention.

A large part of the aforementioned components of the system or the control facility, can be implemented wholly or partially in the form of software modules in a processor of a corresponding computing system. An extensively software-based implementation has the advantage that it is also possible to retrofit computing systems used to date in a simple way via a software update in order to work in the manner according to one or more example embodiments of the present invention. Insofar, the object is also achieved by a corresponding computer program product with a computer program, which can be loaded directly into a computing system, with program sections for executing steps of the method according to one or more example embodiments of the present invention when the program is executed in the computing system. In addition to the computer program, a computer program product of this kind can optionally comprise additional constituents, such as, for example, documentation and/or additional components, including hardware components, such as, for example, hardware keys (dongles etc.) for using the software.

Transportation to the computing system or to the control facility and/or storage on or in the computing system or the control facility can take place via a computer-readable medium, for example a memory stick, a hard disk or another kind of transportable or integrated data carrier on which the program sections of the computer program that can be read and executed by a computing system or a computer unit of the control facility are stored. For this purpose, the computer unit can, for example, have one or more interacting microprocessors or the like.

Further particularly advantageous embodiments and developments of one or more example embodiments of the present invention result from the dependent claims and the following description, wherein the claims of one claim category can also be developed analogously to the claims and descriptions for another claim category and in particular individual features of different exemplary embodiments or variants can be combined to form new exemplary embodiments or variants.

According to a preferred method, the FFS deflection for a recording (of a projection image) is reduced in such a way that the FFS deflection is reduced to zero for the relevant recordings. Therefore, the FFS control data are preferably constructed such that no FFS deflection takes place for this recording.

According to a preferred method, however, simply no recording (of a projection image) can take place. Therefore, here the control data set can comprise beam control data that simply does not switch on the beam for the relevant recording position and thus also no recording (of a projection image) takes place. Theoretically, for this purpose, in the step of the method in which FFS control data is generated, additionally or alternatively to the FFS control data, beam control data can be generated for the relevant recording(s), which, in the event of cross-radiation being present for the recording (of a projection image), causes an intensity that is reduced relative to a specified intensity of the X-ray beam (can also be zero) for this recording, and otherwise causes the specified intensity.

According to a preferred method, the specified FFS deflection has an FFS starting point and an FFS end point between which the focal point is moved during the FFS movement. Prior to a recording the focal point "jumps" to the FFS starting point and then moves continuously to the FFS end point, in particular wherein the focal point is stationary in space (relative to the detector).

To reduce the FFS deflection, with the reduced FFS deflection, the FFS starting point is now preferably shifted closer to the FFS end point and/or the FFS end point is shifted closer to the FFS starting point. Thus, the distance covered from the focal point on the anode is shortened. Since cross-radiation often occurs in the region of the normal FFS starting point or FFS end point, shifting these points toward one another eliminates this problem. This shortening can be used for FFS deflection in two ways.

In the first way, with the reduced FFS deflection, the movement time of the focal point between the FFS starting point and FFS end point is preferably equal to the specified FFS deflection. Since the distance is shorter, the focal point is therefore guided more slowly. This achieves less "smearing" of the X-ray beam on the detector with effective suppression of cross-radiation.

Alternatively, with the reduced FFS deflection, the speed of the focal point between the FFS starting point and FFS end point is preferably equal to the specified FFS deflection and FFS deflection only takes place after a specified waiting time after the start of the relevant recording (of a projection image) and/or with a pause at the end of the recording. Therefore, when there is a waiting time and a pause, the focal point first moves on the circular path during the waiting time, and then is stationary in space during its FFS deflection and then moves again then on the circular path during the pause. With this alternative, it is also preferable for the X-ray beam to be switched off during the waiting time and/or the pause. Although this does result in a shorter recording time, it has the advantage that the recorded images are optimally movement-compensated.

Preferably, herein, the FFS starting point at an angle to one side (for example, the right) of the vertical over the detector substantially corresponds to the FFS end point at the corresponding angle to the other side (for example, the left) of the vertical, and vice versa.

According to a preferred method, in the event of cross-radiation being present, beam control data for reducing the intensity of the X-ray beam (i.e., its applied dose) for this recording (of a projection image) is added to the control data set. For this purpose, the intensity is reduced with respect to the (previously known) intensity used for a recording. It should be noted that cross-radiation mostly occurs at relatively large angles to the vertical above the detector. If FFS deflection is reduced there, the recording quality is also not optimal, since the beam is "smeared" due to the movement of the X-ray source. If the intensity is now reduced for these images, on the one hand, a lower dose is applied in the over-radiated region and, on the other hand, this can improve calcium visibility. Therefore, there are definite advantages in reducing the applied dose for the outer projections (large angles) and increasing it (or not reducing it) for the middle projections.

According to a preferred method, the control data set additionally comprises aperture control data for tracking the collimator aperture of the X-ray source (during recording) according to the FFS deflection of the focal point. This aperture control data is preferably configured to move the collimator aperture in the form of two movements:
  a return movement in the direction of the circular movement of the X-ray source when the X-ray beam is switched off, wherein, after the X-ray beam is switched off, the collimator aperture is moved to a starting position relative to the X-ray source,
  continuous tracking against the direction of the circular movement of the X-ray source when the X-ray beam is switched on, wherein the collimator aperture is tracked from the starting position to an end position, preferably wherein the collimator aperture is tracked such that it substantially has a constant position with respect to a line between the focal point and a predetermined point on the detector, preferably with respect to the center of the detector.

Prior to the recording (of a projection image), therefore, the collimator aperture "jumps" to the starting position, is then continuously tracked during the FFS deflection, for example so that it is stationary in space together with the focal point, and then jumps back to the new starting position. This has the advantage that cross-radiation can be more effectively prevented by this movement of the collimator aperture since the beam cone can be more effectively directed from the focal point onto the detector.

Theoretically, in the step of the method in which FFS control data is generated, additionally or alternatively to the FFS control data, aperture control data can be generated for the relevant recording(s), which, in the event of cross-radiation being present for the recording (of a projection image), can achieve a movement of the collimator aperture. The movement is such that the collimator aperture describes a path in which a simulated beam geometry no longer has cross-radiation or the cross-radiation is below a threshold value.

According to a preferred method, during its continuous tracking, the collimator aperture is moved such that during the movement of the X-ray source relative
  to the detector and/or
  to a focal point and/or
  to a point of intersection of a line between the focal point and a predetermined point on the detector with a plane of the collimator aperture, it is stationary or moves more slowly than the orbital speed of the circular movement toward or counter to the circular movement, or moves with a time offset to the FFS deflection.

In this respect, the relative movement of the focal point and detector is fairly important for an optimal result.

In the event of the specified FFS deflection taking place during a recording (of a projection image), the focal point is normally stationary in space relative to the detector. For an optimal result, here, the collimator aperture should also be stationary in space (as should the point of intersection). However, in the event, of reduced FFS deflection taking place, the focal point can first move in space (at its FFS starting point) then be stationary (during the reduced FFS movement) and then move again (at its FFS end point), or it is tracked with a reduced distance and thus moves in space more slowly than the circular movement. In this case, the collimator aperture should preferably also move in space, namely relative to the focal point or, preferably, relative to the point of intersection.

However, there can also be a deliberately non-synchronous movement of the collimator aperture with the focal point, wherein the collimator aperture is moved at a different speed than the focal point (more slowly or more quickly) or with a time lag in order to compensate only a part of the cross-radiation.

According to a preferred method, the collimator aperture is only continuously tracked when FFS deflection takes place, in particular only when current flows through the FFS deflection coil and/or (only) when the X-ray source is switched on.

According to a preferred method, a change to the aperture opening of the collimator aperture takes place during the recording of different projection images, preferably wherein the further the angle of the X-ray source deviates from the vertical to the detector, the smaller the aperture opening. This change to the aperture opening can take place with or without tracking of the collimator aperture and has the advantage that cross-radiation can be better prevented with a smaller aperture at large angles of the focal point to the vertical above the detector.

A preferred method comprises the additional steps:
  producing a plurality of projection images, wherein the X-ray beam of the X-ray source is turned on and off many times during its circular movement,
  FFS deflection of the focal point during the production of the projection recordings according to the control data set, preferably wherein, in the event of FFS deflection, the focal point is guided counter to the circular movement of the X-ray source.

According to a preferred method, after the production of the projection images, a number of images (for example slice images) are reconstructed from the recorded projection images. During the reconstruction, data from projection images is preferably weighted differently based on the control data set (depending on the spatial frequency). Herein, in particular the greater the reduction of the FFS deflection was, the lower the weighting.

BRIEF DESCRIPTION OF THE DRAWINGS

The present invention is described again in more detail in the following with reference to the attached figures and with reference to exemplary embodiments. Herein, the same components are given identical reference symbols in the different figures. The figures are generally not to scale. They show.

DETAILED DESCRIPTION

Figure 1:
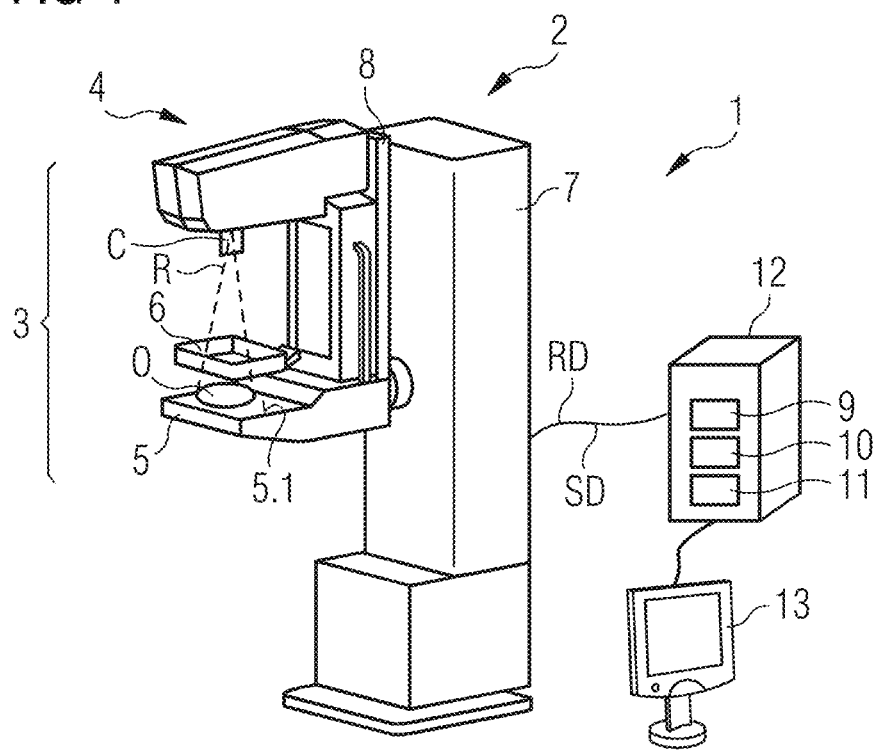
FIG. 1 a rough schematic representation of a preferred tomosynthesis system with a preferred system, FIG. 2 an example of an X-ray source with a system according to one or more example embodiments of the present invention, FIG. 3 an example of FFS deflection, FIG. 4 an example of a recording without FFS deflection according to the prior art, FIG. 5 an example of a recording with FFS deflection, FIG. 6 a flow chart for a possible sequence of a method according to one or more example embodiments of the present invention.

FIG. 1 is a rough schematic representation of an example of a tomosynthesis system 1. Relative directional information such as "above", "below" etc. refer to a tomosynthesis system 1 set up for operation as intended. The tomosynthesis system 1 comprises a tomosynthesis device 2 and a control facility 12. The tomosynthesis device 2 has an upright column 7 and a source-detector arrangement 3, which in turn comprise an X-ray source 4 and a detector 5 with a detector surface 5.1. The upright column 7 stands on the floor during operation. The source-detector arrangement 3 is movably connected thereto, so that the height of the detector surface 5.1, i.e., the distance to the floor, can be adjusted to a patient's breast height.

A breast O of the patient (here represented schematically) lies on top of the detector surface 5.1 as an examination object O for an examination. A plate 6, which is movably connected to the source-detector arrangement 3, is arranged above the breast O and the detector surface 5.1. For the examination, the breast O is compressed and at the same time fixed by lowering the plate 6 onto it so that pressure is exerted on the breast O between the plate 6 and detector surface 5.1.

The X-ray source 4 is arranged and embodied opposite the detector 5 such that the detector 5 detects X-rays R emitted thereby after at least some of the X-rays R have penetrated the patient's breast O. Herein, the X-ray source 4 can be swiveled relative to the detector 5 via a rotary arm 8 in a range of ±50° about a basic position in which it is perpendicular to the detector surface 5.1.

The control facility 12 receives the raw data RD from the measurement and sends control data SD to the tomosynthesis device 2. It is connected to a terminal 13 via which a user can communicate commands to the tomosynthesis system 1 or retrieve measurement results. The control facility 12 can be arranged in the same room as the tomosynthesis device 2, but it can also be located in an adjacent control room or at an even greater spatial distance.

The system 20 according to one or more example embodiments of the present invention (see also FIG. 2) comprises a simulation unit 9, a determining unit 10 and a control data unit 11.

The simulation unit 9 is configured to simulate a beam geometry of the X-ray beam R at a specified FFS deflection onto the detector 5 during recording of a projection image P.

The determining unit 10 is configured to determine whether cross-radiation is present in a predetermined region around the detector 5 by the simulated X-ray beam R.

The control data unit 11 is configured to generate a control data set D. In this respect, it is able to generate FFS control data DF and preferably also beam control data DS and aperture control data DB (see FIG. 2) for the recording. In the event of cross-radiation being present for the recording (of a projection image P), the control data set D comprises FFS control data DF which causes FFS deflection for this recording that is reduced relative to a specified FFS deflection, and otherwise comprises FFS control data DF that causes a specified FFS deflection.

Further details relating to the function of the units are also set forth below with respect to FIG. 6.

Figure 2:
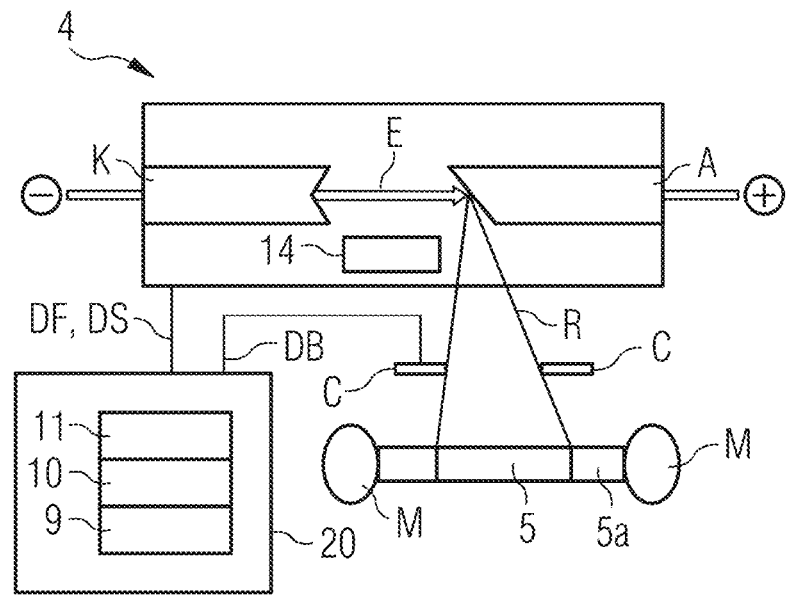

FIG. 2 is a schematic representation of an X-ray source 4. A cathode K and an anode A are arranged in an airless housing (of the actual X-ray tube) between which, during the operation of the X-ray source 4, an electron beam E is accelerated and hits the anode A.

To enable the point of impact of the electron beam E on the anode A to be changed, an FFS deflection coil 14 is arranged between the cathode K and anode A and has the effect of FFS deflection of the electron beam E. If a deflection current is applied thereto, it generates a magnetic field in which the electron beam E is deflected. Here, the deflection takes place in dependence on the polarity of the deflection current either into or out of the image plane. While the X-ray source 4 is moved on a circular path (see for example FIG. 5) and an X-ray beam R is emitted in one direction, the electron beam E can be deflected with the FFS deflection coil 14.

The X-ray source 4 emits an X-ray beam R through a collimator aperture C onto a flat X-ray detector 5 with peripheral regions 5a on which two arms are depicted as body parts M of a person M, wherein the electron beam E in the X-ray source 4 can be deflected via the FFS deflection coil 14.

The FFS deflection in the X-ray source 4 is achieved with a system according to one or more example embodiments of the present invention, as already described in more detail above (see FIG. 1). This deflection takes place into the image plane and out of the image plane.

Here, both FFS control data DF and beam control data DS and aperture control data DB are sent from the system 20, wherein the FFS control data DF acts on the FFS deflection, the beam control data DS acts on the beam intensity of the X-ray beam R and the aperture control data DB acts on a movement of the collimator aperture C.

Figure 3:
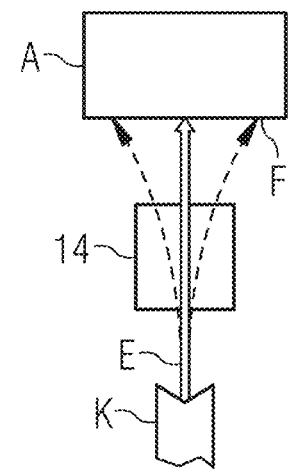

The top view in FIG. 3 represents the deflection of the electron beam E in this X-ray source 4.

Figure 4:
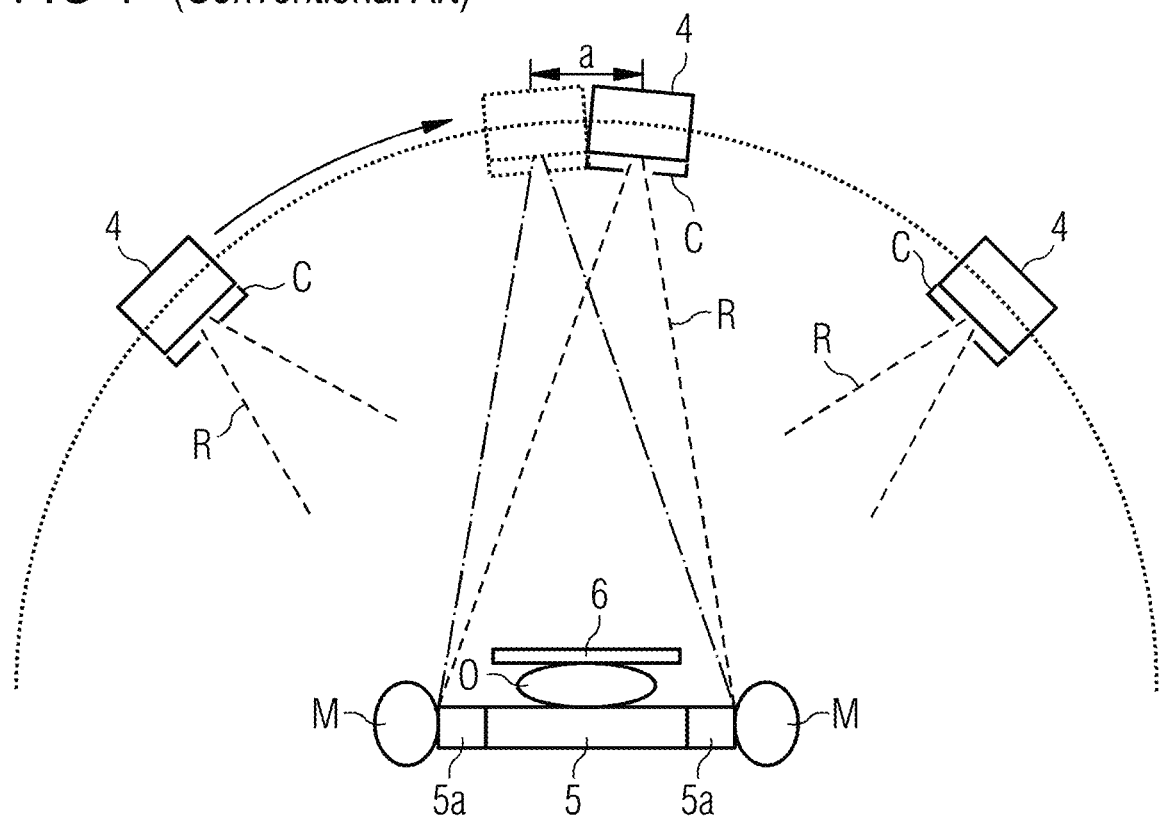

FIG. 4 shows the movement of an X-ray source 4 of an FFS X-ray system 1 according to FIG. 1 during a tomosynthesis examination according to the prior art. During the examination, the X-ray source 4, guided by the rotary arm 8, moves continuously on a circular arc along the arrow and radiates an X-ray beam R, which is collimated by a collimator aperture C, onto the object O to be examined on the detector 5. Meanwhile, during this continuous movement, a plurality of X-ray projections or "X-ray shots" are recorded with the detector 5.

As indicated at the central position, during an X-ray projection that lasts for a certain time, the X-ray source 4 moves along a distance a. Here, the central position during the X-ray projection is shown as solid and the starting and end positions are shown as dotted (the X-ray projection takes place between the starting and end position). Thus, during recording (of a projection image P), the angle of the X-ray beam R moves resulting in smearing of the recorded image.

This motion artifact is avoided by FFS tracking, which always keeps the focal point in the central position (indicated as solid).

Figure 5:
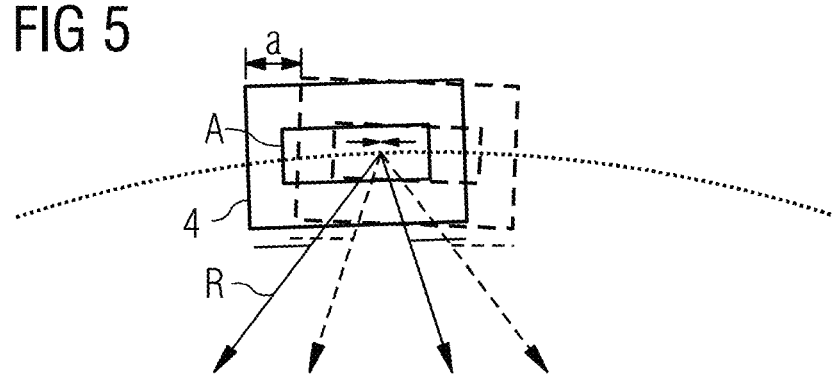

FIG. 5 shows an example of FFS tracking during a tomosynthesis examination. Once again, this depicts the uppermost point of the circular path with the starting position (here shown as solid) and the end position (dotted) of the X-ray source 4 in which here the anode A is also indicated. FFS deflection causes the electron beam E, which here hits the anode A from above in the image plane, to be first deflected toward the right and later toward the left (arrows) so that the point of impact on the anode A (focal point) always remains at one position in space throughout the entire movement of the X-ray source 4 during this X-ray projection.

Figure 6:
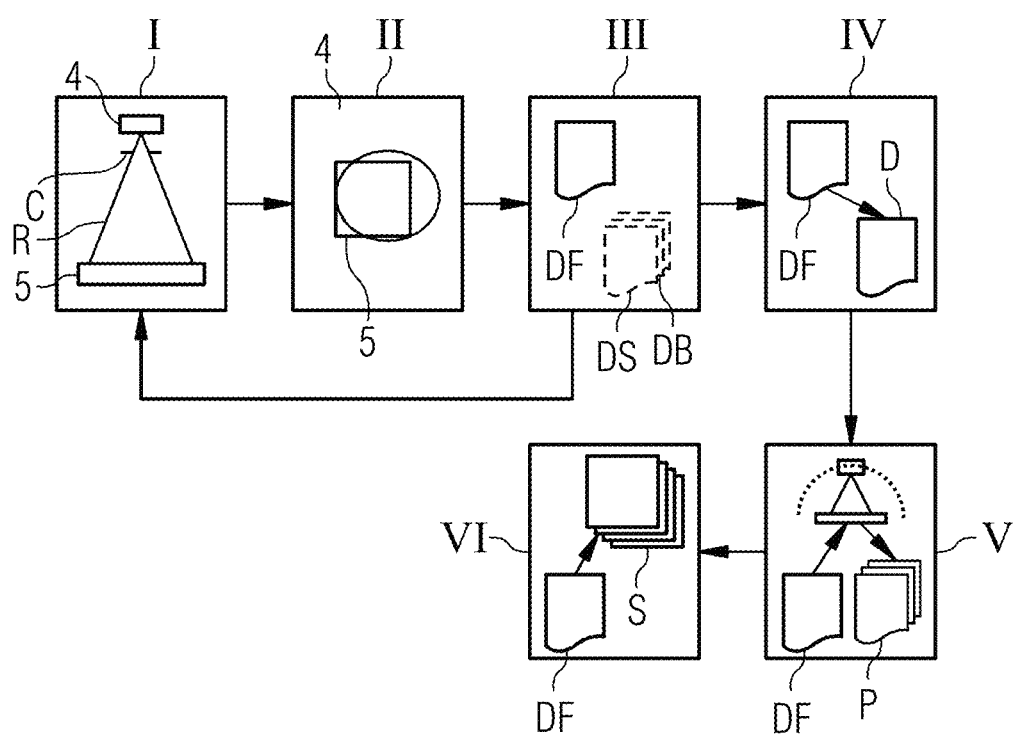

FIG. 6 shows a flow chart for a possible sequence of a method according to one or more example embodiments of the present invention for controlling an FFS X-ray system 1 as shown, for example, in FIG. 1. Herein, in this example, not only is a control data set D generated, which on its own already enables control, but also an image is recorded and reconstructed.

First, step I is a simulation of the beam geometry of the X-ray beam R at a specified FFS deflection onto the detector 5 during recording of a projection image P. Herein, the projection image does not have to be actually recorded since all the necessary information is available.

Step II is the determination as to whether cross-radiation is present in a predetermined region around the detector 5 by the simulated X-ray beam R. This shows the detector 5 from above (square) and an irradiated region (circle) on the detector 5. As can be seen, the circle extends beyond the edges of the detector, which corresponds to cross-radiation.

Step III is the generation of FFS control data DF for recording (of a projection image P), which, in the event of cross-radiation being present for the recording, causes FFS deflection that is reduced relative to the specified FFS deflection for this recording, and otherwise causes the specified FFS deflection.

Dashed lines indicate that it is additionally possible to generate aperture control data DB for tracking a collimator aperture C and/or beam control data DS for regulating the intensity of the X-ray beam R.

These steps are now repeated for all recordings (positions of the X-ray source 4 during the recordings).

Step IV is the generation of a control data set D comprising the generated FFS control data DF and possibly additionally the generation of aperture control data DB and/or beam control data DS for controlling an FFS X-ray system 1.

Step V is the production (recording) of a plurality of projection images P, wherein the X-ray beam R of the X-ray source 4 is turned on and off many times during its circular movement.

Meanwhile, FFS deflection of the focal point F takes place according to the control data set D, wherein, in the event, the focal point F is stationary in space, possibly partially.

Step VI is a reconstruction of slice images S from the recorded projection images P, wherein during the reconstruction, data from projection images P is weighted differently on the control data set D, wherein, the greater the reduction of the FFS deflection was, the lower the weighting.

Reference is made once again to the fact that the method described above in detail and system depicted are only exemplary embodiments which can be modified by the person skilled in the art in wide ranges without departing from the scope of the present invention. Furthermore, the use of the indefinite article "a" or "an" does not preclude the possibility that the features in question may also be present on a multiple basis. Similarly, terms such as "unit" do not preclude the possibility that the components in question could consist of multiple interacting sub-components, which could also be spatially distributed. The expression "a number" should be understood as meaning "at least one".

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A method for controlling an FFS X-ray system including an X-ray source, which is guided in a circular movement around a detector to produce a plurality of projection images, wherein an X-ray beam collimated by a collimator aperture is turned on and off repeatedly during the circular movement, and wherein, for an FFS deflection, the FFS X-ray system includes an FFS deflection coil with which a focal point of an electron beam generating the X-ray beam is deflectable between a cathode and an anode of the X-ray source, wherein the method comprises:
    simulating a beam geometry of the X-ray beam at a specified FFS deflection onto the detector during a recording of a projection image;
    determining whether cross-radiation is present in a region around the detector by the simulated beam geometry of the X-ray beam;
    generating FFS control data for the recording of the projection image, wherein
        the FFS control data either (i) causes the FFS deflection that is reduced relative to the specified FFS deflection for the recording of the projection image in an event of the cross-radiation being present for the recording of the projection image, or (ii) causes the specified FFS deflection otherwise;
    repeating the simulating, the determining, and the generating FFS control data for at least one further recording of a projection image; and
    generating a control data set, including the FFS control data, for controlling the FFS X-ray system.

2. The method as claimed in claim 1, wherein the FFS deflection for the recording of the projection image is reduced such that the FFS deflection is reduced to zero for relevant recordings or no recording of a projection image takes place.

3. The method as claimed in claim 1, wherein
the specified FFS deflection has an FFS starting point and an FFS end point between which the focal point of the electron beam is moved, and
to reduce the FFS deflection, at least one of the FFS starting point is shifted closer to the FFS end point, or the FFS end point is shifted closer to the FFS starting point.

4. The method as claimed in claim 3, wherein
a movement time of the focal point of the electron beam between the FFS starting point and the FFS end point with the reduced FFS deflection is equal to the specified FFS deflection, or
a speed of movement of the focal point of the electron beam between the FFS starting point and the FFS end point with the reduced FFS deflection is equal to the specified FFS deflection, and the FFS deflection only takes place after at least one of a specified waiting time after a start of the recording of image or with a pause at an end of the recording of a projection image.

5. The method as claimed in claim 4, wherein
the FFS starting point at an angle to a first side of a vertical above the detector substantially corresponds to the FFS end point at a corresponding angle to a second side of the vertical.

6. The method as claimed in claim 1, wherein in the event of the cross-radiation being present, the method further comprises:
adding, to the control data set, beam control data for reducing an intensity of the X-ray beam for the recording of a projection image.

7. The method as claimed in claim 1, wherein
the control data set includes aperture control data for tracking the collimator aperture according to the FFS deflection,
the aperture control data is configured to
move the collimator aperture in a return movement in a direction of the circular movement of the X-ray source when the X-ray beam is switched off, wherein after the X-ray beam is switched off, the collimator aperture is moved to a starting position relative to the X-ray source, or
move the collimator aperture in a continuous tracking movement against the direction of the circular movement of the X-ray source when the X-ray beam is switched on, wherein
the collimator aperture is tracked from the starting position to an end position.

8. The method as claimed in claim 7, wherein, during the continuous tracking movement, the method comprises:
moving the collimator aperture such that, during the circular movement of the X-ray source relative to at least one of the detector, the focal point of the electron beam, or a point of intersection of a line between the focal point of the electron beam and a point on the detector with a plane of the collimator aperture, the collimator aperture (i) is stationary, (ii) moves slower than an orbital speed of the circular movement toward or counter to the circular movement, or (iii) moves with a time offset to the FFS deflection.

9. The method as claimed in claim 7, wherein the collimator aperture is only continuously tracked when the FFS deflection occurs.

10. The method as claimed in claim 7, further comprising:
changing an aperture opening of the collimator aperture, wherein
the aperture opening decreases as an angle of the X-ray source deviates from a vertical to the detector.

11. The method as claimed in claim 7, wherein the collimator aperture is tracked such that the collimator aperture has a substantially constant position with respect to a line between the focal point of the electron beam and a point on the detector.

12. The method as claimed in claim 11, wherein the point on the detector is at a center of the detector.

13. The method as claimed in claim 7, wherein the collimator aperture is only continuously tracked at least one of (i) when a current flows through the FFS deflection coil, or (ii) when the X-ray source is switched on.

14. The method as claimed in claim 1, further comprising:
producing the plurality of projection images, wherein
the X-ray beam is turned on and off repeatedly during the circular movement; and
guiding the focal point of the on beam counter to the circular movement of the X-ray source in an event of an FFS deflection of the focal point of the electron beam during a production of the plurality of projection images.

15. The method as claimed in claim 14, further comprising:
reconstructing a number of images from the plurality of projection images, wherein
during a reconstruction, data from the plurality of projection images is weighted differently based on the control data set.

16. The method as claimed in claim 15, wherein as a reduction of the FFS deflection increases, the weighting decreases.

17. A non-transitory computer-readable medium storing program sections that, when executed by at least one processor, cause the at least one processor to perform the method as claimed in claim 1.

18. A system for controlling an FFS X-ray system including an X-ray source, which is guided in a circular movement around a detector to produce a plurality of projection images, wherein an X-ray beam collimated by a collimator aperture is turned on and off repeatedly during the circular movement, and wherein, for an FFS deflection, the FFS X-ray system includes an FFS deflection coil with which a focal point of an electron beam generating the X-ray beam is deflectable between a cathode and an anode of the X-ray source, the system comprising:
a simulation unit configured to simulate a beam geometry of the X-ray beam at a specified FFS deflection onto the detector during a recording of a projection image;
a determining unit configured to determine whether cross-radiation is present in a region around the detector by the simulated beam geometry of the X-ray beam; and
a control data unit configured to generate a control data set including FFS control data for the recording of the projection image, wherein
the FFS control data either (i) causes the FFS deflection that is reduced relative to the specified FFS deflection for the recording of the projection image in an event of the cross-radiation being present for the recording of the projection image, or (ii) causes the specified FFS deflection otherwise.

19. An X-ray system comprising:
the system as claimed in claim 18, and
an X-ray device including the X-ray source and the detector, wherein, the system is configured to control the X-ray device.

20. The X-ray system as claimed in claim 19, wherein the X-ray device is a mammography device.

21. A system for controlling an FFS X-ray system including an X-ray source, which is guided in a circular movement around a detector to produce a plurality of projection images, wherein an X-ray beam collimated by a collimator aperture is turned on and off repeatedly during the circular movement, and wherein, for an FFS deflection, the FFS X-ray system includes an FFS deflection coil with which a focal point of an electron beam generating the X-ray beam is deflectable between a cathode and an anode of the X-ray source, the system comprising:

processing circuitry configured to:
simulate a beam geometry of the X-ray beam at a specified FFS deflection onto the detector during a recording of a projection image,
determine whether cross-radiation is present in a region around the detector by the simulated beam geometry of the X-ray beam, and
generate a control data set including FFS control data for the recording of the projection image, wherein the FFS control data either (i) causes the FFS deflection that is reduced relative to the specified FFS deflection for the recording of the projection image in an event of the cross-radiation being present for the recording of the projection image, or (ii) causes the specified FFS deflection otherwise.

\* \* \* \* \*